(12) United States Patent
Kelly (10) Patent No.: US 10,335,261 B2
(45) Date of Patent: Jul. 2, 2019

(54) VESSEL FILTER AND METHODS FOR USE (71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days.

(21) Appl. No.: 15/130,195

(22) Filed: Apr. 15, 2016

(65) Prior Publication Data

US 2016/0302909 A1    Oct. 20, 2016

Related U.S. Application Data (60) Provisional application No. 62/148,737, filed on Apr. 16, 2015.

(51) Int. Cl.
*A61F 2/01* (2006.01)

(52) U.S. Cl.
CPC ......... *A61F 2/013* (2013.01); *A61F 2002/011* (2013.01); *A61F 2002/016* (2013.01);
(Continued)

(58) Field of Classification Search
CPC .......... A61F 2/01; A61F 2/013; A61F 2/0063; A61F 2002/011; A61F 2002/016;
(Continued)

(56) References Cited

U.S. PATENT DOCUMENTS 4,877,030 A * 10/1989 Beck ................... A61F 2/92
606/195
5,007,926 A * 4/1991 Derbyshire ............ A61F 2/92
606/191

(Continued)

FOREIGN PATENT DOCUMENTS

WO    02/055123 A2    7/2002
WO    14/199381 A2    12/2014
WO    2015104645 A2    7/2015

OTHER PUBLICATIONS

Carpenter, Jeffrey P. "Reducing the risk of stroke and embolic lesions of TEVAR and TAVI with embolic protection devices." Vascular News, Nov. 10, 2015. available at at www.vascularnews.com/vn-features/vascular-news---feature/reducing-the-risk-of-stroke-and-embolic-lesions-of-tevar-and-tavi-with-embolic-protection-devices?highlight=carpenter%20November%2010,%202015 as of Apr. 14, 2016.

(Continued)

*Primary Examiner* — Dianne Dornbusch
(74) *Attorney, Agent, or Firm* — McDonnell Boehnen Hulbert & Berghoff LLP (57) ABSTRACT An apparatus and methods for use are provided, where the apparatus includes: (a) a filter, and (b) a frame having a first end and a second end, wherein the frame includes a first support and a second support extending between the first end and the second end, wherein at least the first support and the second support of the frame are coupled to at least a portion of a periphery of the filter, wherein the frame and the filter together define a lumen, wherein the frame has shape memory and is movable between a first position in which the lumen has a first diameter and a second position in which the lumen has a second diameter, and wherein the first diameter is smaller than the second diameter.

27 Claims, 7 Drawing Sheets (52) U.S. Cl.
CPC ............... *A61F 2210/0014* (2013.01); *A61F 2230/0067* (2013.01); *A61F 2250/0067* (2013.01)

(58) Field of Classification Search
CPC ...... A61F 2002/0068; A61F 2002/0072; A61F 2220/00
See application file for complete search history.

(56) References Cited

U.S. PATENT DOCUMENTS

| | | | | |
|---|---|---|---|---|
| 5,330,500 | A * | 7/1994 | Song | A61F 2/90 606/198 |
| 5,368,602 | A * | 11/1994 | de la Torre | A61B 17/0057 602/44 |
| 5,383,926 | A * | 1/1995 | Lock | A61F 2/92 606/198 |
| 5,824,046 | A * | 10/1998 | Smith | A61F 2/07 623/1.13 |
| 5,824,082 | A * | 10/1998 | Brown | A61F 2/0063 623/11.11 |
| 6,090,996 | A * | 7/2000 | Li | A61L 31/044 606/151 |
| 6,139,573 | A * | 10/2000 | Sogard | A61F 2/07 623/1.13 |
| 6,149,681 | A * | 11/2000 | Houser | A61F 2/07 623/1.12 |
| 6,156,062 | A * | 12/2000 | McGuinness | A61F 2/82 606/198 |
| 6,312,463 | B1 * | 11/2001 | Rourke | A61F 2/01 623/1.2 |
| 6,451,047 | B2 * | 9/2002 | McCrea | A61F 2/06 623/1.13 |
| 6,613,074 | B1 * | 9/2003 | Mitelberg | A61B 17/12022 606/200 |
| 6,613,078 | B1 * | 9/2003 | Barone | A61F 2/07 606/194 |
| 6,929,659 | B2 * | 8/2005 | Pinchuk | A61F 2/07 623/1.13 |
| 7,381,222 | B2 * | 6/2008 | Pflueger | A61F 2/203 128/848 |
| 7,524,332 | B2 * | 4/2009 | Osborne | A61F 2/2418 623/2.14 |
| 7,647,931 | B2 * | 1/2010 | Pflueger | A61F 2/203 128/848 |
| 7,758,606 | B2 * | 7/2010 | Streeter | A61F 2/01 606/200 |
| 7,771,382 | B2 * | 8/2010 | Levine | A61F 5/0079 604/8 |
| 7,918,882 | B2 * | 4/2011 | Pavcnik | A61B 17/12022 604/9 |
| 8,388,650 | B2 * | 3/2013 | Gerberding | A61B 17/12022 606/157 |
| 8,470,022 | B2 * | 6/2013 | Johnson | A61F 2/2415 600/36 |
| 8,545,530 | B2 * | 10/2013 | Eskridge | A61B 17/12022 606/191 |
| 8,551,132 | B2 * | 10/2013 | Eskridge | A61B 17/12022 606/191 |
| 2001/0044651 | A1 * | 11/2001 | Steinke | A61F 2/915 623/1.16 |
| 2002/0138129 | A1 * | 9/2002 | Armstrong | A61F 2/07 623/1.11 |
| 2004/0010308 | A1 * | 1/2004 | Zafrir-Pachter | A61F 2/82 623/1.35 |
| 2006/0241675 | A1 * | 10/2006 | Johnson | A61F 2/01 606/200 |
| 2006/0271097 | A1 * | 11/2006 | Ramzipoor | A61B 17/12022 606/200 |
| 2007/0198059 | A1 * | 8/2007 | Patel | A61B 17/0057 606/213 |
| 2008/0027477 | A1 * | 1/2008 | Obermiller | A61B 17/0057 606/191 |
| 2008/0119886 | A1 * | 5/2008 | Greenhalgh | A61B 17/0057 606/200 |
| 2008/0147111 | A1 * | 6/2008 | Johnson | A61F 2/01 606/200 |
| 2009/0254172 | A1 * | 10/2009 | Grewe | A61F 2/856 623/1.15 |
| 2010/0050581 | A1 * | 3/2010 | Schuld | B01D 46/0005 55/503 |
| 2011/0082536 | A1 * | 4/2011 | Cook | A61L 31/10 623/1.15 |
| 2012/0046739 | A1 * | 2/2012 | von Oepen | A61F 2/915 623/2.11 |
| 2014/0031857 | A1 | 1/2014 | Richardson | |
| 2014/0046358 | A1 * | 2/2014 | Cully | A61F 2/01 606/200 |
| 2014/0228843 | A1 * | 8/2014 | O'Donnell | A61B 18/1492 606/48 |
| 2014/0249566 | A1 | 9/2014 | Quinn | |
| 2014/0330303 | A1 * | 11/2014 | Hansen | A61B 17/12109 606/200 |
| 2014/0343598 | A1 * | 11/2014 | Johanson | A61F 2/01 606/200 |
| 2015/0119977 | A1 * | 4/2015 | Parodi | A61F 2/013 623/2.11 |
| 2015/0173884 | A1 * | 6/2015 | Johnson | A61F 2/01 606/200 |

OTHER PUBLICATIONS

International Search Report for corresponding PCT application No. PCT/US2016/027777, dated Jun. 20, 2016.

* cited by examiner

VESSEL FILTER AND METHODS FOR USE

RELATED APPLICATIONS

This application claims priority U.S. Provisional Application No. 62/148,737 entitled "Vessel Filter and Methods for Use," filed on Apr. 16, 2015, which is hereby incorporated by reference in its entirety.

BACKGROUND OF THE INVENTION

Cardiovascular surgery has traditionally been performed with open surgical techniques. These techniques typically involve invasive procedures to surgically excise diseased tissue before sewing in an artificial replacement, which may often require prolonged clamping to halt blood flow through the diseased segment. These open surgical techniques can only be performed on relatively healthy patients and often result in relatively long recovery periods. Recently, minimally invasive techniques have been developed and used with endovascular or catheter-directed methodologies. However, minimally invasive techniques can create a new set of complications that need to be dealt with, such as embolus formation.

In several diseased states, the cardiovascular system may develop thrombus buildup. One area where thrombus buildup is troublesome is the aortic arch. If blood flow from the heart is not hemodynamically normal, it can result in thrombus deposition throughout the arch. This can be a result of aortic valve stenosis creating regurgitation and subsequent turbulent flow in the aortic arch. Alternatively, it could be caused by aneurysmal dilation which causes slower than normal velocities as well as regions along the curvature of the bulge where recirculating zones and stagnation develop, which lead to further thrombus formation.

In order to repair the large cardiovascular structures near the heart, relatively large catheter systems often need to be advanced across the aortic arch. These larger catheter systems are relatively stiff, so they may require additional force to advance around the curvature of the arch. The relative stiffness of the catheter may bias the catheter toward the outer curvature of the arch, and the resulting forces generated can break emboli free when the catheter is advanced through thrombotic regions.

Once broken free, there are three main sets of outlets through which such emboli may travel: the great vessels, the visceral branch vessels, or the distal/lower extremities. Emboli travelling to the distal extremities can be marginally problematic. Emboli travelling through the great vessels to the arms can also be marginally problematic. But emboli travelling through the great vessels to the brain could result in a stroke. Further, emboli travelling to the branch vessels of the visceral segment could be very problematic as well, because emboli can cause bowel ischemia which can be deadly. As the size and number of emboli increase, they become more problematic.

SUMMARY OF THE INVENTION

The present invention is directed to an apparatus configured to prevent emboli from entering the three great vessels of the aortic arch, especially emboli having a diameter greater than about 100 μm. The apparatus beneficially provides a working lumen that may allow for ongoing perfusion, as well as for treatment upstream of the apparatus while the apparatus is in place.

Thus, in a first aspect, the present invention provides an apparatus including (a) a filter, and (b) a frame having a first end and a second end, wherein the frame includes a first support and a second support extending between the first end and the second end, wherein at least the first support and the second support of the frame are coupled to at least a portion of a periphery of the filter, wherein the frame and the filter together define a lumen, wherein the frame has shape memory and is movable between a first position in which the lumen has a first diameter and a second position in which the lumen has a second diameter, and wherein the first diameter is smaller than the second diameter.

In a second aspect, the present invention also provides a method comprising: (a) delivering the apparatus of the first aspect to a target vessel via a catheter, and (b) advancing the apparatus out of the catheter and thereby expanding the frame of the apparatus due to shape memory and conforming the frame and the filter to the target vessel.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Exemplary apparatus and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed apparatus and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means+/−5%.

As used herein, "target vessel" refers to the blood vessel or artery in which the apparatus is deployed. The target vessel may further include artificial lumens used, for example, as teaching aids.

As used herein, the "filter" refers to a material that may effectively permit blood flow through the filter but prevent particles having a given diameter or greater from passing therethrough.

As used herein, the "frame" refers to a structure capable of having shape memory that comprises a bio-compatible material.

Figure 1:
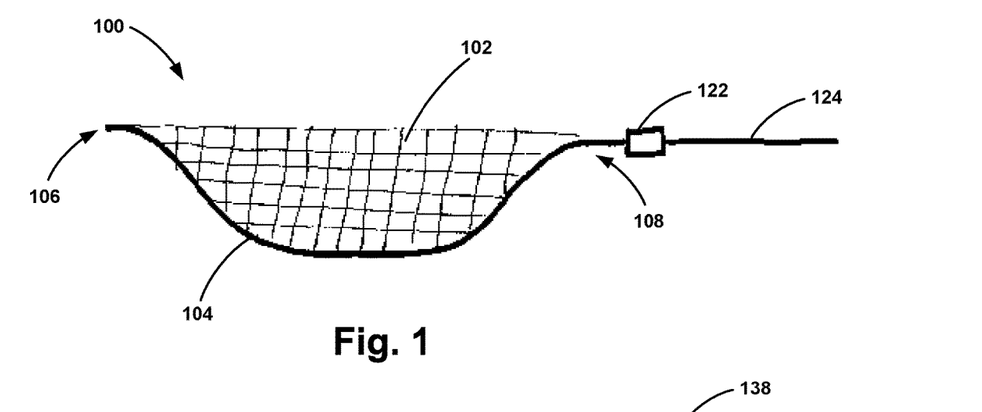
FIG. 1 illustrates a side view of an apparatus, according to an example embodiment.
Figure 2:
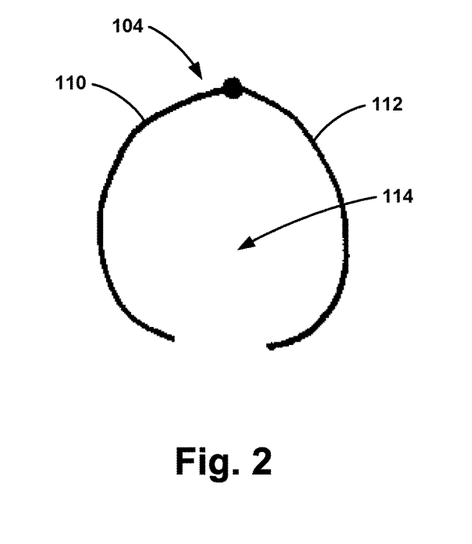
FIG. 2 illustrates a front view of the apparatus, according to the embodiment of FIG. 1.
Figure 3:
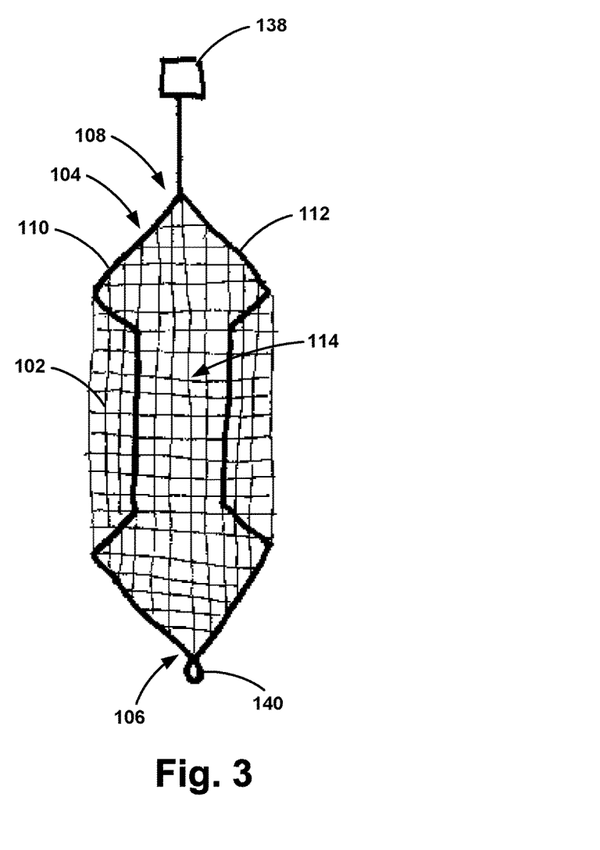
FIG. 3 illustrates a top view of the apparatus, according to the embodiment of FIG. 1, in a second expanded position.

With reference to the Figures, FIG. 1 is a side view of an example apparatus 100. As shown in FIG. 1, the apparatus 100 may include a filter 102 and a frame 104 having a first end 106 and a second end 108. FIG. 2 is a front view of the example apparatus 100, and FIG. 3 is a bottom view of the apparatus 100. As shown in FIGS. 2 and 3, the frame 104 includes a first support 110 and a second support 112 extending between the first end 106 and the second end 108. As shown in FIG. 3, the first support 110 and the second support 112 of the frame 104 are coupled to at least a portion of a periphery of the filter 102. The frame 104 and the filter 102 together define a lumen 114. The frame 104 has shape memory and is movable between a first position in which the lumen 114 has a first diameter and a second position in which the lumen has a second diameter, where the first diameter is smaller than the second diameter. In one embodiment, the first position corresponds to a compressed pre-deployment configuration of the apparatus 100 and the second position corresponds to an expanded post-deployment configuration of the apparatus 100. The frame 104 may have a length from the first end 106 to the second end 108 ranging from about 30 mm to about 250 mm.

Figure 5:
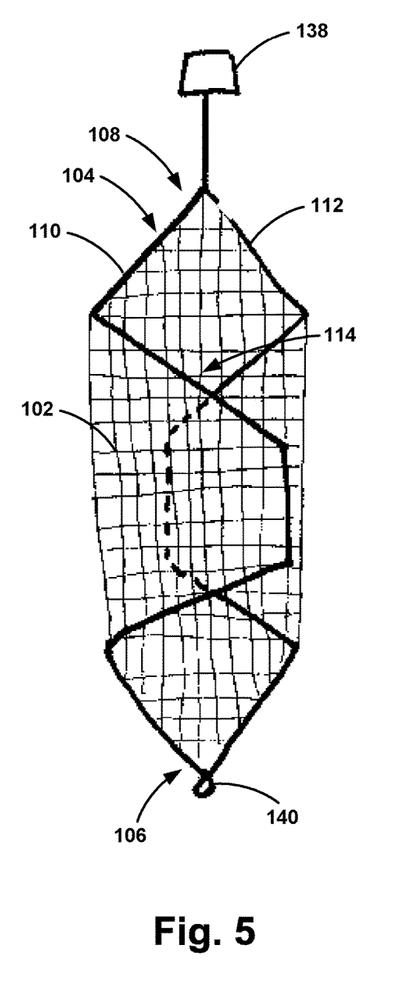
FIG. 5 illustrates a top view of the apparatus according to the embodiment of FIG. 1, in a first compressed position.

As shown in FIG. 5, in the first position, at least a portion of the filter 102 coupled to the first support 110 and at least a portion of the filter 102 coupled to the second support 112 may overlap each other along a length of the first support 110 and a length of the second support 112. This arrangement enables the apparatus 100 to be compressed.

Figure 4:
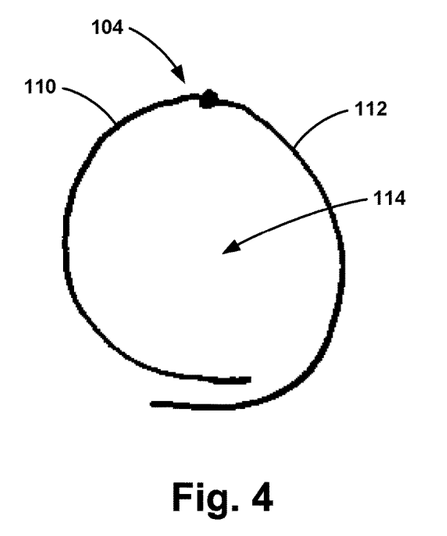
FIG. 4 illustrates a front view of an apparatus, according to an example embodiment.
Figure 6:
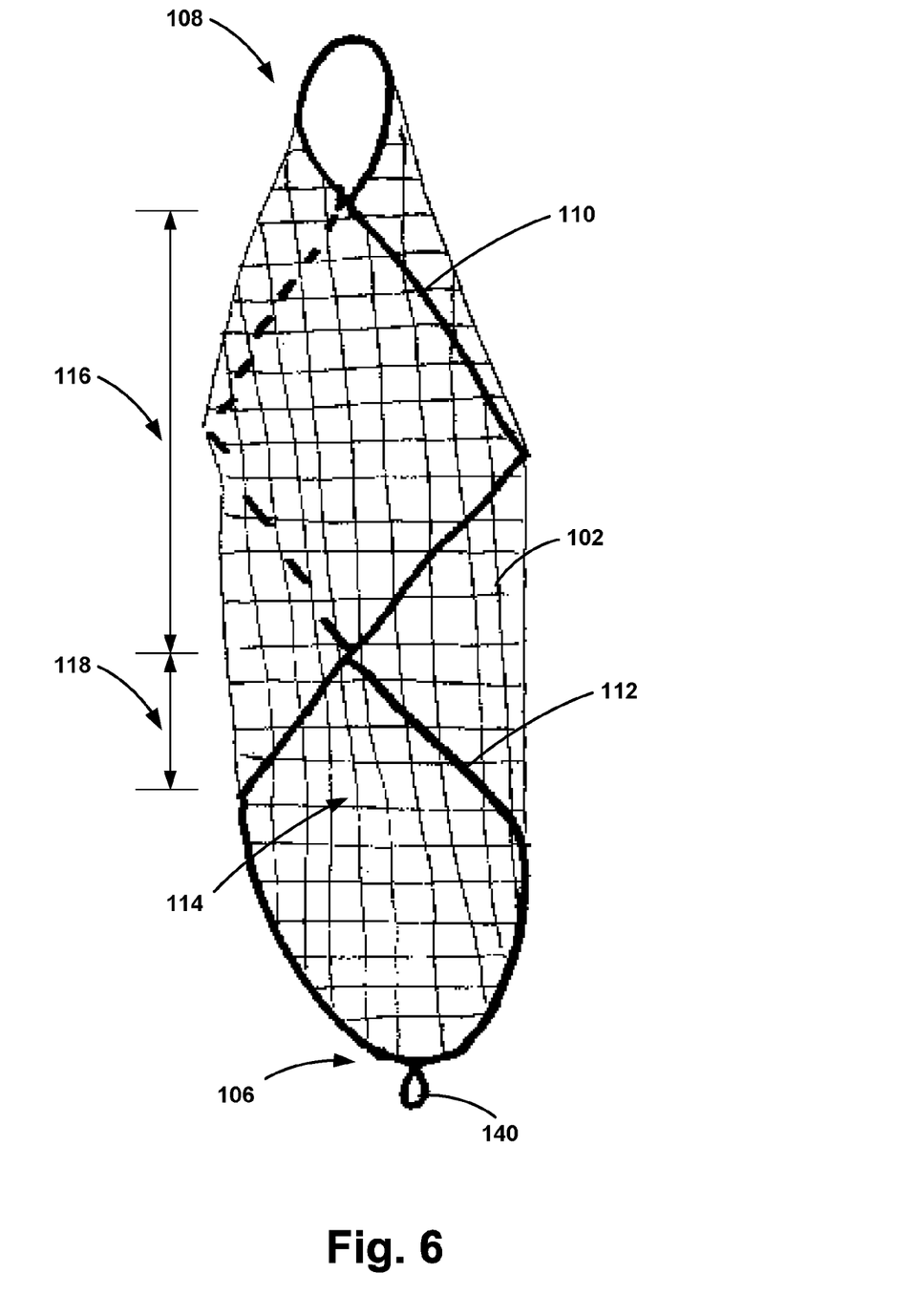
FIG. 6 illustrates a top view of an apparatus, according to an example embodiment.

The second position may take a variety of forms. In one example, such as the configuration shown in FIGS. 4 and 5, in the second position at least a portion of the filter 102 coupled to the first support 110 and at least a portion of the filter 102 coupled to the second support 112 overlap each other along the length of the first support 110 and the length of the second support 112. In such an example, a smaller portion of the filter 102 will overlap in the second position compared with the first position. In another example, such as the configuration shown in FIGS. 2 and 3, in the second position at least a portion of the filter 102 coupled to the first support 110 and at least a portion of the filter 102 coupled to the second support 112 are arranged spaced apart such that there is a gap between the first support 110 and the second support 112. In yet another example, such as the configuration shown in FIG. 6, in the second position at least a portion of the filter 102 coupled to the first support 110 and at least a portion of the filter 102 coupled to the second support 112 have an overlapping region 116 and a spaced apart region 118. In the second position, the lumen 114 defined by the frame 104 and the filter 102 may have a diameter ranging from about 5 mm to about 160 mm.

In one example, the frame 104 is coupled to the filter 102 along the entire periphery of the filter 102. In use, the filter 102 is configured to prevent the passage therethrough of particles having a given diameter. In various embodiments, the filter 102 may prevent the passage therethrough of particles having a diameter greater than about 10 μm, greater than about 50 μm, greater than about 100 μm, greater than about 250 μm, or greater than about 500 μm.

Further, the filter 102 may have a thickness ranging from about 0.001 mm to about 0.5 mm. The filter 102 may be porous, cross-hatched, or multi-layered. In one particular example, the filter 102 may be made of such bio-compatible materials as polyethylene terephthalate (PET) knit fabric, dacron, polyester, polycaprolactone, polyethylene, polypropylene, polyvinylchloride, polyethersulfone, polylactide, polyglycolide, polyethersulfone, polyetrafluoroethylene, polyetheretherketone, polysulfone, and/or polypropylene. In one example, the filter material may be sewn to the shape memory frame 104 using a polyester surgical suture with polybutalate coating or other suitably bio-compatible suture materials. In another example, the filter material may be bonded to the shape memory frame 104 using radiofrequency bonding, among other bonding techniques. Other means to provide positive fixation of the filter 102 to the frame 104 are possible as well.

In another example, the filter 102 may comprise a plurality of shape memory wires. Such shape memory wires may comprise nitinol, titanium, titanium alloys, or copper-aluminum-nickel alloys as examples. In such an example, the shape memory wires may be woven together in a cross-hatch pattern to form the filter 102. In another example, the plurality of shape memory wires may be disposed within the filter material to form the filter 102. In such an example, the plurality of shape memory wires may be curved to bias the frame 104 in the second position.

In one example, the first support 110 and the second support 112 comprise the same type of shape memory material, such as nitinol, titanium, titanium alloys, or copper-aluminum-nickel alloys as examples. In another example, the first support 110 may comprise a first shape memory material, while the second support 112 may comprise a second shape memory material that is different than the first shape memory material. In yet another example, the first support 110 and the second support 112 may have different thicknesses or diameters to thereby impart different forces on the target vessel during deployment.

The filter 102 may be disposed on the frame 104 in such a way that it prevents materials from entering one or more branches of the aortic arch. Therefore, if there is some slack and the filter 102 begins to bow when implanted in vivo, it would be advantageous if the filter 102 bowed outward toward the outer curve of the aortic arch. There are several ways in which this may be accomplished. For instance, the flow of blood to the great vessels might bow the filter 102 outward toward the outer curve of the arch. Additionally, there may be a hook 113 (shown in FIG. 11) attached to the filter material that could be captured with a snare wire from one of the great vessels, preferably the brachiocephalic artery 142. In such an example, once snared, gentle tensile force can be applied to the snare wire during critical maneuvers of the procedure to ensure that any emboli that break free during the maneuver are caught because the filter 102 is in the proper configuration to protect the branches of the aortic arch.

Figure 7:
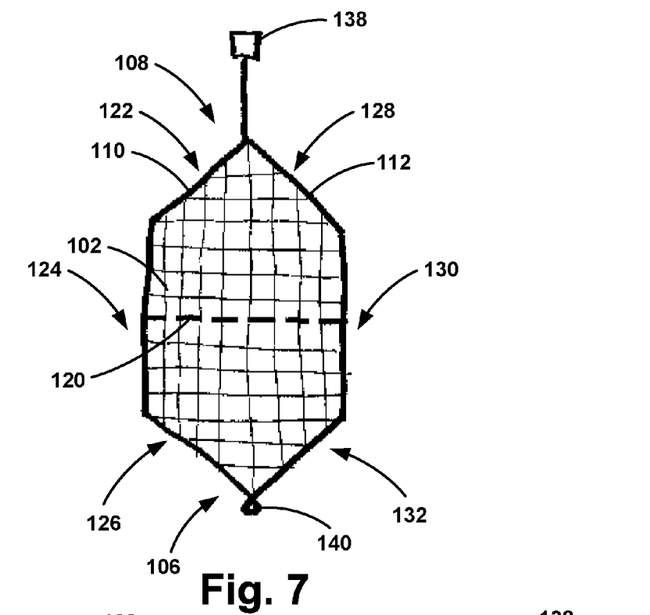
FIG. 7 illustrates a top view of an apparatus, according to an example embodiment.
Figure 8:
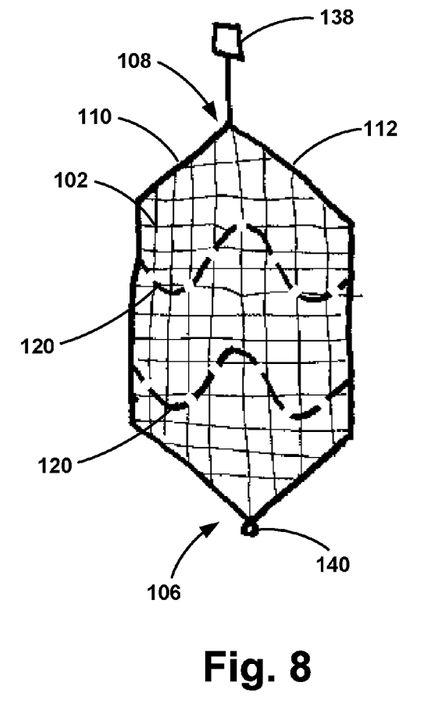
FIG. 8 illustrates a top view of an apparatus, according to an example embodiment.
Figure 9:
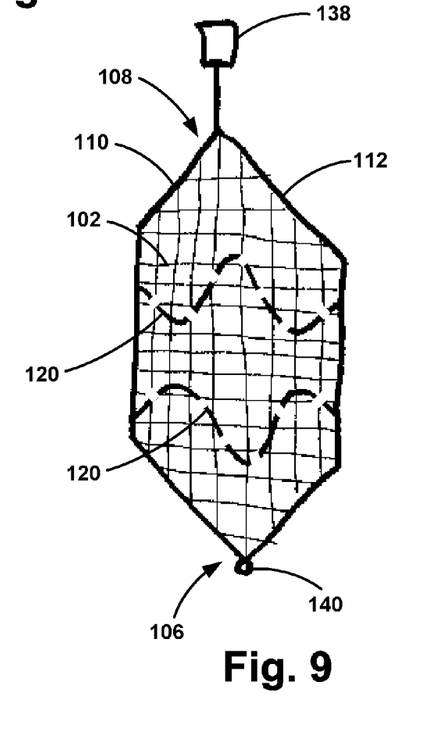
FIG. 9 illustrates a top view of an apparatus, according to an example embodiment.

In another embodiment, the apparatus 100 may include a lateral support 120 extending between the first support 110 and the second support 112. Such an embodiment is shown in FIG. 7. The lateral support 120 may include a shape memory material configured to bias the frame 104 to the second position. The shape memory material of the lateral support 120 may comprise nitinol, titanium, titanium alloys, or copper-aluminum-nickel alloys as examples. In one example, as shown in FIG. 7, the lateral support 120 is curved such that a center of the lateral support 120 extends towards the filter. In such an example, the lateral support 120 may provide an additional force to position the filter 102 against the surface of the target vessel. In another example, as shown in FIGS. 8 and 9, the lateral support 120 is sinusoidal in shape. Further, as shown in FIGS. 8 and 9, more than one lateral support 120 may be present. The sinusoidal shape of the lateral support 120 may improve filter 102 apposition to the target vessel wall. In addition, the lateral support 120 may help apply uniform concentric pressure to the target vessel wall thus minimizing the risk of creating a dissection.

In yet another embodiment, the frame 104 may include a first torsion spring 140 arranged at the first end 106 of the frame 104. Further, the frame 104 may include a second torsion spring (not shown) arranged at the second end 108 of the frame 104. The first and second torsion springs may bias the frame 104 to the second position to aid in the expansion of the frame 104 and the filter 102 during deployment in the target vessel. Further, the first and second torsion springs may help seal the first end 106 and the second end 108 of the frame 104 against the target vessel wall.

As shown in FIGS. 7-9, the frame 104 and filter 102 of the apparatus 100 may taper and narrow from the first support 110 and the second support 112 to the second end 108 of the frame 104. Further, the frame 104 and the filter 102 of the apparatus 100 may taper and narrow from the first support 110 and the second support 112 to the first end 106 of the frame 104. In particular, as shown in FIG. 7, the first support 110 may include a first angled section 122, a first substantially straight section 124, and a second angled section 126. Further, as shown in FIG. 7, the second support 112 may include a third angled section 128, a second substantially straight section 130, and a fourth angled section 132. In one example, the first substantially straight section 124 and the second substantially straight section 130 may comprise a different material than one or more of the angled sections 122, 126, 128, 132. In another example, the first substantially straight section 124 and the second substantially straight section 130 may have a different thickness or diameter than one or more of the angled sections 122, 126, 128, 132. In one particular example, the thickness or diameter of the first substantially straight section 124 and the second substantially straight section 130 may be greater than the thickness of the first angled section 122 and the third angled section 128, to ease re-sheathing of the apparatus 100 after use.

Figure 10:
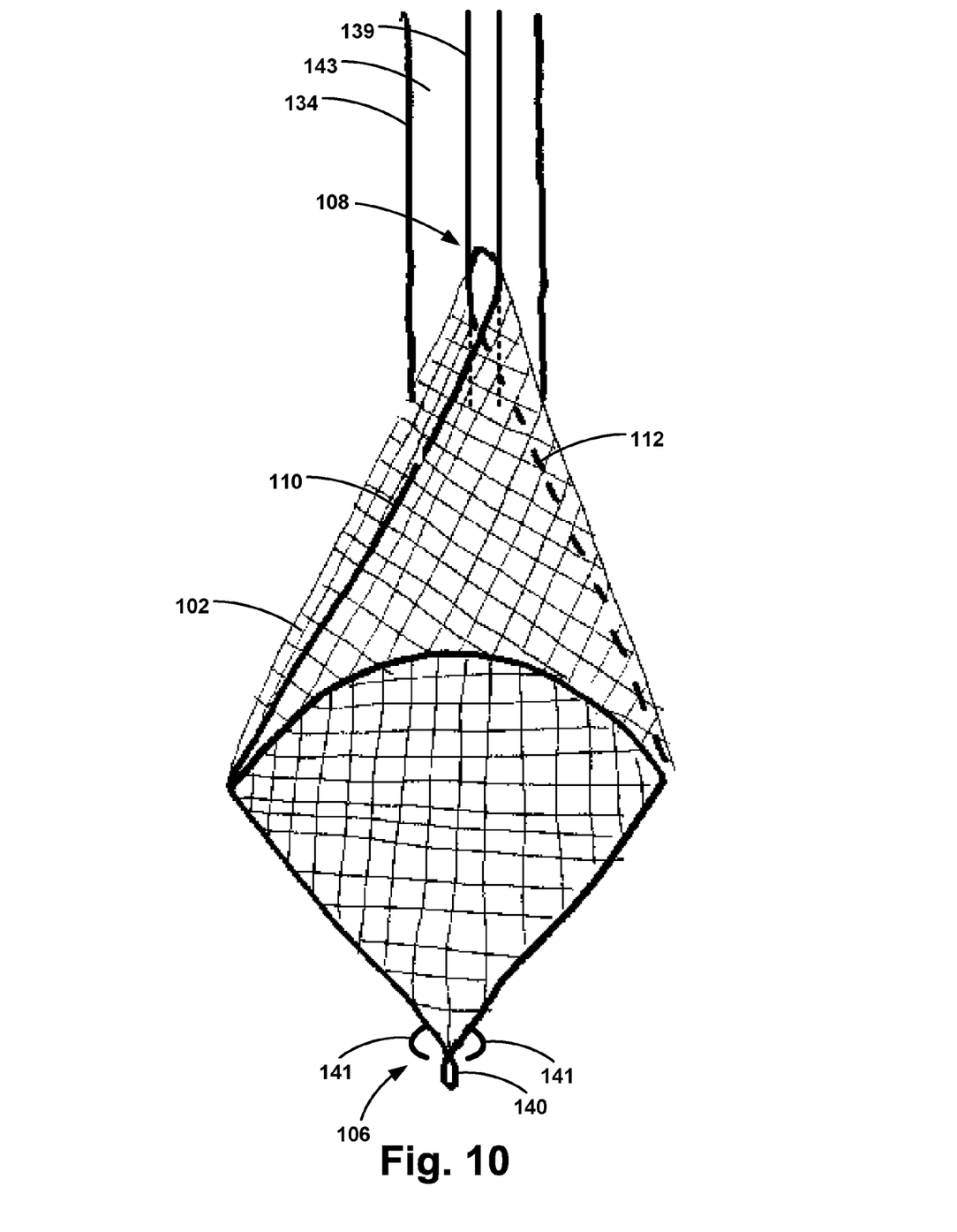
FIG. 10 illustrates a top view of an apparatus, according to an example embodiment.

As shown in FIG. 10, such an arrangement the tapered second end 108 of the frame 104 and filter 102 permits the frame 104 and the filter 102 to form a cone-shape at the second end 108 when the second end 108 of the frame 104 is advanced back into the catheter 134. As such, the frame 104 may have an intermediate position such that the frame 104 and the filter 102 define the cone-shape at the second end 108 of the frame 104 when the frame 104 transitions between the first position and the second position. This capability may beneficially capture emboli particles that break away from the filter 102 during re-sheathing in the cone-shaped second end 108 of the apparatus 100, thereby preventing those particles from entering the bloodstream.

In another example, the apparatus 100 may further include a deployment shaft 136 coupled to the second end 108 of the frame 104. The deployment shaft 136 may be detachable from the frame 104 via a coupling mechanism 138. The coupling mechanism 138 may take a variety of forms. In one example, the coupling mechanism 138 may include male and female mating threads. The male and female portions of the mating threads may be made from a bio-compatible metal such as titanium, nitinol or a hard bio-compatible polymer, as examples. Once the filter 102 is deployed, the catheter shaft 134 can be twisted in order to detach the catheter 134 from the apparatus 100. In another example, the coupling mechanism 138 may include a releasable pull cord within the deployment shaft 136. In another example, the coupling mechanism 138 may include wiring configured to impart an electric charge to a coupling between the second end 108 of the frame 104 and the deployment shaft 136. In yet another example, the coupling mechanism 138 may include an inflatable balloon configured to fracture the connection between the deployment shaft 136 and the frame 104 upon inflation. Other example coupling mechanisms are possible as well.

In one embodiment, the first end 106 of the frame 104 may include one or more snarable features 141 (shown in FIG. 10), which may be snared by a guide wire from the descending aorta to remove the apparatus 100 from the target vessel after completion of the procedure. Other snarable features can be added to the first end 104 of the filter 102, thereby enabling the operator to pull on a snare wire effectively bending the first end 106 of the frame 104 in the direction of the second end 108 of the frame 104 while the second end 108 of the frame is at least partially positioned within the catheter 134, thereby trapping the emboli in the apparatus 100 for safe removal from the patient. In another embodiment, the apparatus 100 may be detached from the deployment shaft 136 and left in the target vessel to continue filtering after a procedure is completed. In a further embodiment, the filter 102 may dissolve or be absorbed by a patient's body after a period of in vivo exposure.

The apparatus 100 described above may be used in a variety of procedures, such as a transcatheter aortic valve replacement, a mitral clip, or exclusion of an ascending aortic aneurysm or a dissection, as examples. In a transcatheter aortic valve replacement, a catheter is brought form a groin access, through the aorta, over the aortic arch, and into the native valve before deployment. The large size of the valve on the stent is what makes the catheter large in diameter. In a mitral clip, the same approach is used with the catheter advancing through the aortic valve and then through the septum before the mitral valve is clipped. Finally, in an ascending aortic aneurysm or dissection a stent graft is positioned again from the same approach. The stent graft is then deployed above the sinotubular junction and below the braciocephalic artery. Each such procedure requires a relatively large stent graft resulting in a large catheter being advanced up and over the aortic arch, thereby potentially breaking loose thrombus forming dangerous emboli.

During an aortic valve replacement, mitral clip placement, or an ascending aortic aneurysm stent graft placement, cerebral embolic protection may be helpful, as discussed above. To place the apparatus 100 in a target vessel, a guide wire may be advanced through a femoral access, through the iliac artery and aorta, and over the aortic arch. Then the catheter 134 carrying the apparatus 100 may be advanced over the guide wire and positioned within the aortic arch. A radiopaque marker on the catheter can help with positioning. In one particular example, an 'e' shaped marker can be used to ensure that the filter 102 opens in the proper direction with the basket opening up with the mesh extending toward the great vessels. The catheter 134 can slowly be retracted allowing the frame 104 to partially open. Positioning can then be checked and the filter 102 can be repositioned as needed to ensure proper coverage of the great vessels. Then the filter 102 can be fully deployed and the catheter 134 removed from the body.

In another embodiment, the catheter 134 may remain in place while the mitral clip, transcatheter valve, ascending aortic stent graft, or other device is positioned within the patient. In such an example, as shown in FIG. 10, the catheter 134 may include a wire lumen 139 positioned within the lumen 143 of the catheter 134. In operation, the wire lumen 139 may be used to pass a guide wire therethrough to deliver various devices to target vessels downstream of the filter. When the filter 102 is pulled towards the catheter 134, the filter 102 may form a conical shape to capture the emboli and other debris present in the filter 102. Additionally, if the filter 102 collects so much embolic debris that it cannot be fully brought back into the catheter 134, the entire catheter 134 and filter 102 may be removed. Having the wire lumen 139 in the catheter 134 allows for the guide wire to be left behind when the filter 102 is removed so that the operator does not lose wire access once the filter 102 is removed. The wire lumen 139 may be positioned such that even when the filter 102 is pulled towards the catheter 134 and partially inserted within the catheter 134, a guide wire may be positioned through the wire lumen 139 and subsequently through the lumen 114 of the filter 102. As such, the wire lumen 139 enables other devices to be advanced through the catheter 134 at various stages of the procedure.

Figure 11:
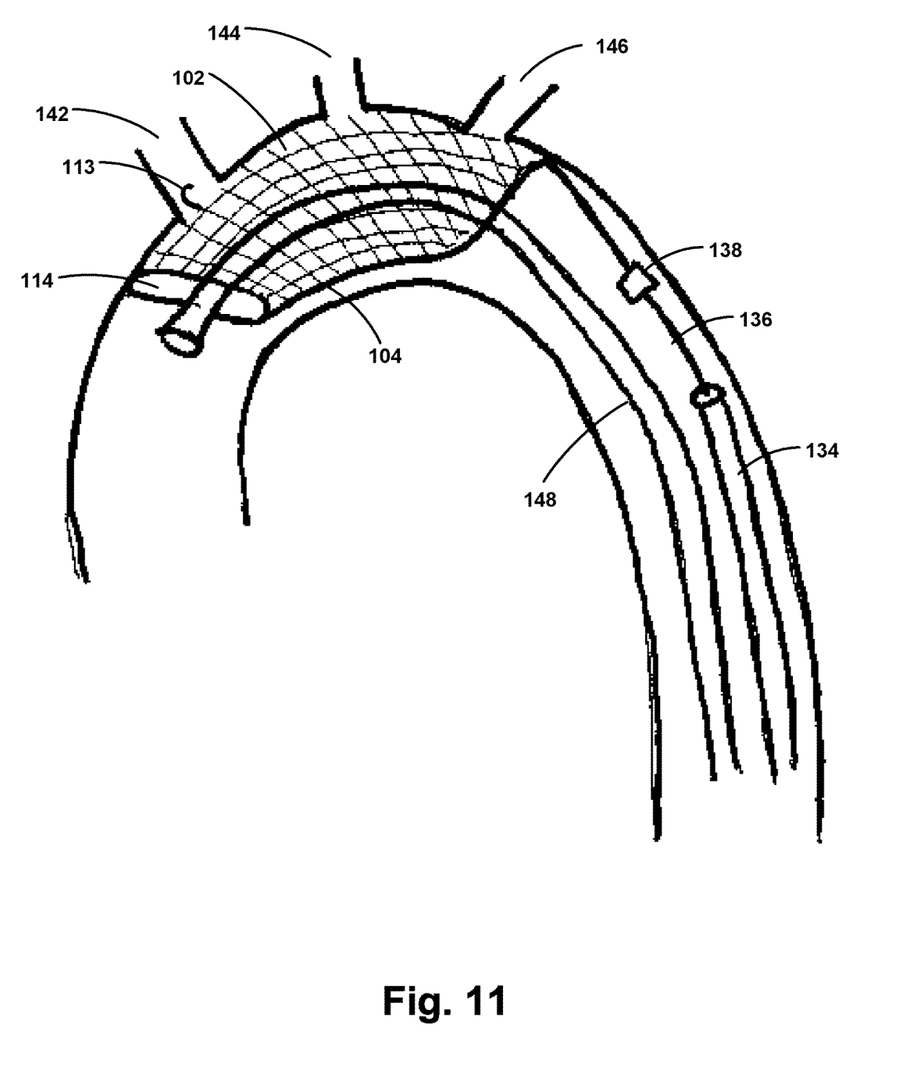
FIG. 11 illustrates a schematic of the cardiopulmonary structure with the filter positioned therein according to an example embodiment.

As shown in FIG. 11, once deployed, the apparatus 100 forms a partial tubular structure through the aorta through which the mitral clip, transcatheter valve, ascending aortic stent graft, or other device can be placed. A delivery catheter 148 is shown positioned through the lumen 114 of the apparatus 100. In the example shown in FIG. 11, the delivery catheter 148 is separate from the catheter 134. In another embodiment, the delivery catheter 148 may be positioned within the lumen 143 of the catheter 134. In such an embodiment, the delivery catheter 148 is a separate lumen within the catheter 134, such that only catheter 134 is positioned within the patient. The tubular structure of the apparatus 100 allows the same groin access to be used for the aortic valve, mitral clip, or stent graft as was used for the apparatus 100. Further, as shown in FIG. 11, once deployed the apparatus 100 is positioned such that the filter 102 covers each of the brachiocephalic artery 142, the left common carotid artery 144, and the left subclavian artery 146.

Once the aortic valve, mitral clip, stent graft, or other device is placed, the apparatus 100 can be removed. Once the catheter is readvanced, the frame 104 may be pulled toward the catheter 134, as shown in FIG. 10. The operator can then snare the first end 106 of the frame 104 from the groin access. Once snared, the first end 106 of the frame 104 can be pulled toward the second end 108 of the frame 104 while the second end 108 of the frame is at least partially positioned within the catheter 134. With the frame 104 pulled partially into the catheter 134, the frame 104 may form a conical shape. Then, as the first end 106 of the filter 104 is pulled towards the second end 108 of the frame 104 by the snare wire, the first end 106 can fold over the opening of the conical shape of the filter 104, effectively trapping the emboli within the conical shape of the frame 104 and filter 102. Once the filter 102 and any ensuing emboli are in the catheter 134 or trapped within the filter 104, they can be removed along with the catheter 134 from the body.

During a branched aortic arch aneurysm repair, the apparatus 100 can be used in an alternative way. In such an example, the apparatus 100 can be advanced over a wire from a groin access similar to the method used during an aortic valve, mitral clip, or ascending stent graft placement. The apparatus 100 may be partially deployed again once being carefully positioned in the aortic arch. If the operator is not pleased with the initial placement, the operator can reposition the apparatus 100 or recapture the apparatus 100 before repositioning. Once comfortable with the position, the operator can fully deploy the filter 102. As discussed above, an 'e' shaped radiopaque marker may be used to ensure the filter 102 opens in the correct direction.

Next, the aortic arch aneurysm can be repaired. Devices which come from the groin can again be advanced through the same access and sheath as the apparatus 100 due to the tubular configuration of the apparatus 100 when deployed. Branched aortic stent grafts require their branch and bridging stents extend from the main body stent graft to the target vessel. Because of this, the aortic stent grafts will need to pass through the filter 102 before being perforated by a wire or outback catheter with a needle. Once the filter 102 has been perforated and the guide wire is placed in the target vessel, the target vessel can be stented with a bridging stent. This process can be repeated for each target vessel the operator plans to stent.

Once all intended branch vessels are stented and the main body configurations are in place with distal seal of the stent graft complete, the filter 102 cannot be removed. In such a configuration, the filter 102 will be detached from the deployment shaft 136 via the coupling mechanism 138 as discussed above. Once the filter 102 is detached, the filter catheter 134, guide wire, and all stent graft catheters and wires can be removed before completing the procedure.

Sometimes stent grafts need to be placed in the descending thoracic or the visceral segment of the aorta. In these instances, in addition to the above mentioned scenarios, emboli may be created that travel to the visceral branch vessels, which can be problematic for the patient. A patient with substantial thrombus formation in the descending thoracic aorta can be especially prone to embolization in their visceral branch vessels. In such an example, the apparatus 100 may be deployed in the branch visceral segment of the descending aorta to cover the branch vessels. In such an example, the apparatus 100 may be deployed over a wire from groin access and could be positioned to cover each of the brachiocephalic artery 142, the left common carotid artery 144, and the left subclavian artery 146.

Figure 12:
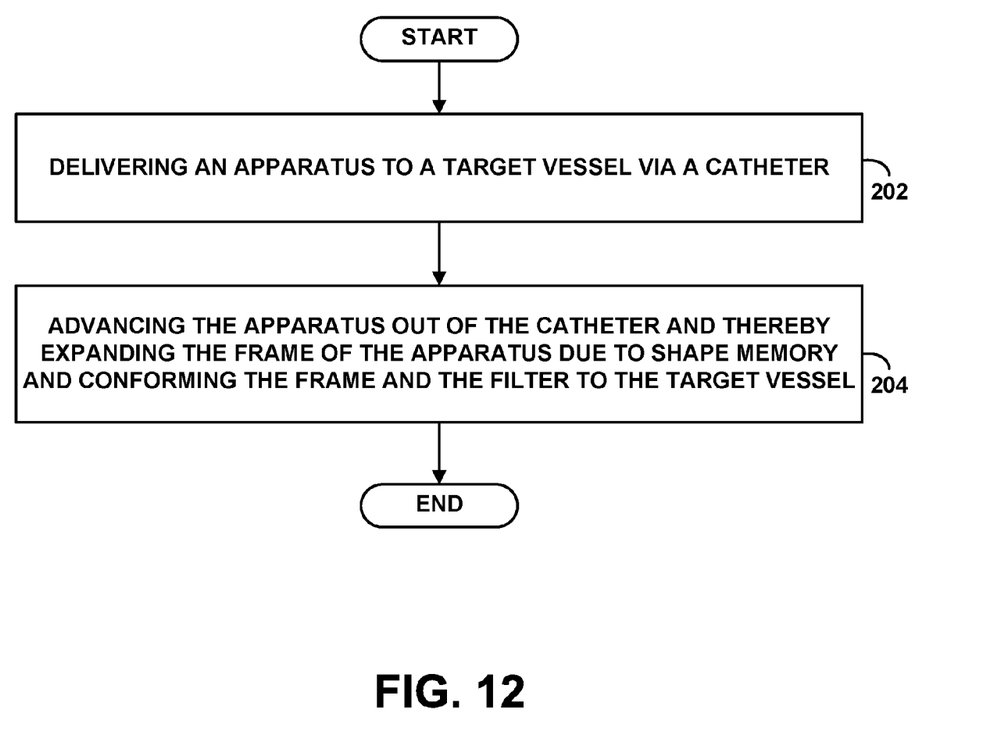
FIG. 12 is a flow chart depicting functions that can be carried out in accordance with example embodiments of the disclosed methods.

FIG. 12 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 202, the method involves delivering an apparatus to a target vessel via a catheter. The apparatus may be the apparatus 100, as described above in relation to FIGS. 1-11. In one example, the target vessel is the aortic arch. In such an example, the method may also include aligning the filter to cover each of the brachiocephalic artery, the left common carotid artery, and the left subclavian artery. At block 204, the method involves advancing the apparatus out of the catheter and thereby expanding the frame of the apparatus due to shape memory and conforming the frame and the filter to the target vessel. In one example, the method may further include the step of advancing the second end of the frame back into the catheter such that the frame and the filter responsively form a cone-shape at the second end.

In another example, the method may further include the step of detaching the second end of the frame from a deployment shaft. In such an example, detaching the second end of the frame from the deployment shaft may comprise unscrewing mating threads of a coupling between the second end of the frame and the deployment shaft. In another example, detaching the second end of the frame from the deployment shaft may comprise imparting an electric charge via wiring of the deployment shaft to a coupling between the second end of the frame and the deployment shaft, and fracturing the coupling via heat from the electric charge. In another example, detaching the second end of the frame from the deployment shaft may comprise inflating a balloon within a coupling between the second end of the frame and the deployment shaft, and fracturing the coupling via pressure from the inflated balloon. In another example, detaching the second end of the frame from the deployment shaft may comprise detaching the second end of the frame from the deployment shaft comprises applying a force to a pull cord within the deployment shaft and separating a coupling between the second end of the frame and the deployment shaft.

In another example, the method may further include the step of snaring the first end of the frame via a snarable feature coupled to the first end of the frame, and pulling the first end of the frame towards the second end of the frame while the second end of the frame is at least partially positioned within the catheter. In such an example, the first end of the frame can be snared and pulled toward the catheter, thereby pulling the first end of the frame in the direction of the second end of the frame and over the conical opening, essentially trapping the embolic material in the filter prior to safely removing from the patient. In yet another embodiment, the method may further include the step of perforating the filter with at least one of a catheter, guide wire, stent, or stent graft.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the following claims.

The invention claimed is:

1. An apparatus comprising:
a filter; and
a frame having a first end and a second end, wherein the frame includes a first support and a second support each continuously extending from the first end to the second end, wherein the first support is coupled to a first side of the filter and the second support is coupled to an opposite side of the filter, wherein the first support is directly coupled to the second support at the first end of the frame such that the frame and the filter taper to a first pointed tip at the first end of the frame, wherein the first support is directly coupled to the second support at the second end of the frame such that the frame and the filter taper to a second pointed tip at the second end of the frame, wherein the frame and the filter together define a first lumen, wherein the frame has shape memory and is movable between a first position in which the first lumen has a first diameter and a second position in which the first lumen has a second diameter, wherein in the second position, the first support and the second support are arranged spaced apart such that there is a gap between the first support and the second support, wherein the first diameter is smaller than the second diameter, wherein the frame and filter together are configured such that an entire length of the apparatus from the first end of the frame to the second end of the frame is configured to be circumferential to a second lumen of a target vessel in the second position, wherein an entire length of the first lumen defined by the frame and the filter is configured to be substantially concentric with the second lumen of the target vessel in the second position, and wherein the frame has an intermediate position such that the frame and the filter define a cone-shape at the second end of the frame such that the first lumen has the first diameter at the second end of the frame and the first lumen has the second diameter at the first end of the frame when the frame transitions from the second position to the first position.

2. The apparatus of claim 1, wherein, in the first position, at least a portion of the filter coupled to the first support and at least a portion of the filter coupled to the second support overlap each other along a length of the first support and a length of the second support.

3. The apparatus of claim 1, further comprising:
at least one lateral support extending between the first support and the second support, wherein the at least one lateral support is configured to bias the frame to the second position.

4. The apparatus of claim 3, wherein the at least one lateral support is curved such that a center of the lateral support extends toward the filter.

5. The apparatus of claim 3, wherein the at least one lateral support is sinusoidal in shape.

6. The apparatus of claim 1, wherein the filter comprises a plurality of shape memory wires.

7. The apparatus of claim 6, wherein the plurality of shape memory wires are woven together in a cross-hatch pattern.

8. The apparatus of claim 6, wherein the plurality of shape memory wires are disposed within a filter media, and wherein the filter media is porous, cross-hatched or multi-layered.

9. The apparatus of claim 6, wherein the plurality of shape memory wires are curved to bias the frame to the second position.

10. The apparatus claim 1, wherein the frame comprises a first torsion spring arranged at the first end of the frame and a second torsion spring arranged at the second end of the frame.

11. The apparatus of claim 1, further comprising:
a deployment shaft coupled to the second end of the frame, wherein the deployment shaft is detachable from the frame.

12. The apparatus of claim 11, wherein the second end of the frame is coupled to the deployment shaft via mating threads or a releasable pull cord.

13. The apparatus claim 11, wherein the deployment shaft comprises wiring configured to impart an electric charge to a coupling between the second end of the frame and the deployment shaft.

14. The apparatus of claim 11, wherein the second end of the frame is coupled to the deployment shaft via a coupling comprising an inflatable balloon such that the coupling is configured to be fracturable by the balloon.

15. The apparatus of claim 1, wherein the first end of the frame is coupled to one or more snarable features.

16. The apparatus of claim 1, wherein the filter is configured to prevent the passage therethrough of particles having a diameter than about 10 µm, greater than about 50 µm, greater than about 100 µm, greater than about 250 µm, or greater than about 500 µm.

17. The apparatus of claim 1, wherein the filter has a thickness ranging from about 0.001 mm to about 0.5 mm.

18. The apparatus of claim 1, wherein the first lumen defined by the frame and the filter in the second position has a diameter ranging from about 5 mm to about 160 mm.

19. The apparatus of claim 1, wherein the length of the frame from the first end to the second end ranges from about 30 mm to about 250 mm.

20. The apparatus of claim 1, wherein the filter comprises material selected from the group consisting of a polyethylene terephthalate (PET) knit fabric, dacron, polyester, polycaprolactone, polyethylene, polypropylene, polyvinylchloride, polyethersulfone, polylactide, polyglycolide, polyethersulfone, polyetrafluoroethylene, polyetheretherketone, polysulfone, and polypropylene.

21. A method comprising:
delivering the apparatus according to claim 1 to a target vessel via a catheter; and
advancing the apparatus out of the catheter and thereby expanding the frame of the apparatus due to shape memory and conforming the frame and the filter to the target vessel.

22. The method of claim 21, further comprising:
advancing the second end of the frame back into the catheter such that the frame and the filter responsively form a cone-shape at the second end.

23. The method of claim 21, further comprising:
detaching the second end of the frame from a deployment shaft.

24. The method of claim 21, further comprising:
snaring the first end of the frame via a snarable feature coupled to the first end of the frame; and
pulling the first end of the frame towards the second end of the frame.

25. The method of claim 21, further comprising:
perforating the filter with at least one of a catheter, a guide wire, a stent, or a stent graft.

26. The method of claim 21, wherein the target vessel is an aortic arch, the method further comprising:
aligning the filter to cover each of the brachiocephalic artery, the left common carotid artery, and the left subclavian artery.

27. The apparatus of claim 1, wherein the frame is configured to be inserted into a catheter to thereby transition the frame from the second position to the first position, and wherein a longitudinal axis of the catheter is configured to be positioned within the second lumen of the target vessel.

* * * * *